(12) United States Patent
Ainsworth et al.

(10) Patent No.: US 8,449,598 B2
(45) Date of Patent: *May 28, 2013

(54) INTRAVASCULAR STENT

(75) Inventors: Stephen D. Ainsworth, Los Gatos, CA (US); E Tina Cheng, San Jose, CA (US); James M. Jacobs, Mountain View, CA (US)

(73) Assignee: Abbott Cardiovascular Systems Inc., Santa Clara, CA (US)

(*) Notice: Subject to any disclaimer, the term of this patent is extended or adjusted under 35 U.S.C. 154(b) by 83 days.

This patent is subject to a terminal disclaimer.

(21) Appl. No.: 13/106,983

(22) Filed: May 13, 2011

(65) Prior Publication Data

US 2011/0213458 A1    Sep. 1, 2011

Related U.S. Application Data

(60) Division of application No. 10/438,687, filed on May 15, 2003, now Pat. No. 7,951,188, which is a continuation of application No. 09/564,151, filed on May 3, 2000, now Pat. No. 6,616,689.

(51) Int. Cl.
*A61F 2/82* (2006.01)

(52) U.S. Cl.
USPC ........................... 623/1.16; 623/1.15

(58) Field of Classification Search
USPC ............. 623/1.1, 1.11, 1.12, 1.13, 1.15, 1.16, 623/1.17, 1.18, 1.19, 1.22, 23.7
See application file for complete search history.

(56) References Cited

U.S. PATENT DOCUMENTS

| | | | |
|---|---|---|---|
| 4,580,568 A | 4/1986 | Gianturco | |
| 5,102,417 A | 4/1992 | Palmaz | |
| 5,104,404 A | 4/1992 | Wolff | |
| 5,292,331 A | 3/1994 | Boneau | |
| 5,449,373 A | 9/1995 | Pinchasik et al. | |
| 5,514,154 A * | 5/1996 | Lau et al. | 623/1.15 |
| 5,607,442 A | 3/1997 | Fischell et al. | |
| 5,632,771 A | 5/1997 | Boatman et al. | |
| 5,643,312 A | 7/1997 | Fischell et al. | |
| 5,669,932 A | 9/1997 | Fischell et al. | |
| 5,674,241 A | 10/1997 | Bley et al. | |
| 5,674,278 A | 10/1997 | Boneau | |

(Continued)

FOREIGN PATENT DOCUMENTS

| DE | 297 08879 U1 | 9/1997 |
|---|---|---|
| EP | 0 088 093 B1 | 1/1986 |

(Continued)

OTHER PUBLICATIONS

Application for U.S. Letters U.S. Appl. No. 09/343,962, filed Jun. 20, 1999.

(Continued)

*Primary Examiner* — David Isabella
*Assistant Examiner* — Suba Ganesan
(74) *Attorney, Agent, or Firm* — Fulwider Patton LLP

(57) ABSTRACT

The invention is directed to an expandable stent for implanting in a body lumen, such as a coronary artery, peripheral artery, or other body lumen. The invention provides for a an intravascular stent having a plurality of cylindrical rings connected by undulating links. The stent has a high degree of flexibility in the longitudinal direction, yet has adequate vessel wall coverage and radial strength sufficient to hold open an artery or other body lumen.

17 Claims, 5 Drawing Sheets

U.S. PATENT DOCUMENTS

| | | |
|---|---|---|
| 5,697,971 A | 12/1997 | Fischell et al. |
| 5,733,303 A | 3/1998 | Israel et al. |
| 5,741,327 A | 4/1998 | Frantzen |
| 5,755,781 A | 5/1998 | Jayaraman |
| 5,776,161 A | 7/1998 | Globerman |
| 5,807,404 A | 9/1998 | Richter |
| 5,810,872 A | 9/1998 | Kanesaka et al. |
| 5,824,040 A | 10/1998 | Cox et al. |
| 5,827,321 A | 10/1998 | Roubin et al. |
| 5,836,964 A | 11/1998 | Richter et al. |
| 5,843,120 A | 12/1998 | Israel et al. |
| 5,843,175 A | 12/1998 | Frantzen |
| 5,853,419 A | 12/1998 | Imran |
| 5,868,781 A | 2/1999 | Killion |
| 5,868,783 A | 2/1999 | Tower |
| 5,876,449 A | 3/1999 | Starck et al. |
| 5,879,370 A | 3/1999 | Fischell et al. |
| 5,879,382 A | 3/1999 | Boneau |
| 5,893,887 A | 4/1999 | Jayaraman |
| 5,911,754 A | 6/1999 | Kanesaka et al. |
| 5,913,895 A | 6/1999 | Burpee et al. |
| 5,922,005 A | 7/1999 | Richter et al. |
| 5,922,020 A | 7/1999 | Klein et al. |
| 5,925,061 A | 7/1999 | Ogi et al. |
| 5,931,866 A | 8/1999 | Frantzen |
| 5,935,162 A | 8/1999 | Dang |
| 5,938,682 A | 8/1999 | Hojeibane et al. |
| 5,938,697 A | 8/1999 | Killion et al. |
| 5,948,016 A | 9/1999 | Jang |
| 5,954,743 A | 9/1999 | Jang |
| 5,964,798 A | 10/1999 | Imran |
| 5,967,986 A | 10/1999 | Cimochowski et al. |
| 5,968,093 A | 10/1999 | Kranz |
| 5,972,018 A | 10/1999 | Israel et al. |
| 5,980,552 A | 11/1999 | Pinchasik et al. |
| 5,993,489 A | 11/1999 | Lewis et al. |
| 6,001,125 A | 12/1999 | Golds et al. |
| 6,004,348 A | 12/1999 | Banas et al. |
| 6,013,091 A | 1/2000 | Ley et al. |
| 6,017,365 A | 1/2000 | Von Oepen |
| 6,019,789 A | 2/2000 | Dinh et al. |
| 6,022,371 A | 2/2000 | Killion |
| 6,022,374 A | 2/2000 | Imran |
| 6,033,433 A | 3/2000 | Ehr et al. |
| 6,033,435 A | 3/2000 | Penn et al. |
| 6,039,755 A | 3/2000 | Edwin et al. |
| 6,039,756 A | 3/2000 | Jang |
| 6,042,597 A | 3/2000 | Kveen et al. |
| 6,042,606 A | 3/2000 | Frantzen |
| 6,048,361 A | 4/2000 | Von Oepen |
| 6,051,020 A | 4/2000 | Goicoechea et al. |
| 6,053,940 A | 4/2000 | Wijay |
| 6,053,941 A | 4/2000 | Lindenberg et al. |
| 6,053,943 A | 4/2000 | Edwin et al. |
| 6,056,775 A | 5/2000 | Borghi et al. |
| 6,056,776 A | 5/2000 | Lau et al. |
| 6,059,822 A | 5/2000 | Kanesaka et al. |
| 6,063,113 A | 5/2000 | Kavteladze et al. |
| 6,066,168 A | 5/2000 | Lau et al. |
| 6,066,169 A | 5/2000 | McGuinness |
| 6,068,656 A | 5/2000 | Von Oepen |
| 6,071,298 A | 6/2000 | Lashinski et al. |
| 6,077,297 A | 6/2000 | Robinson et al. |
| 6,080,191 A | 6/2000 | Summers |
| 6,083,259 A | 7/2000 | Frantzen |
| 6,086,604 A | 7/2000 | Fischell et al. |
| 6,086,611 A | 7/2000 | Duffy et al. |
| 6,090,127 A | 7/2000 | Globerman |
| 6,093,199 A | 7/2000 | Brown et al. |
| 6,093,203 A | 7/2000 | Uflacker |
| 6,099,455 A | 8/2000 | Columbo et al. |
| 6,099,559 A | 8/2000 | Nolting |
| 6,099,560 A | 8/2000 | Penn et al. |
| 6,099,561 A | 8/2000 | Alt |
| 6,102,940 A | 8/2000 | Robichon et al. |
| 6,106,548 A | 8/2000 | Roubin et al. |
| 6,113,627 A | 9/2000 | Jang |
| 6,113,628 A | 9/2000 | Borghi |
| 6,117,165 A | 9/2000 | Becker |
| 6,123,721 A | 9/2000 | Jang |
| 6,129,754 A | 10/2000 | Kanesaka et al. |
| 6,129,755 A | 10/2000 | Mathis et al. |
| 6,152,957 A | 11/2000 | Jang |
| 6,156,052 A | 12/2000 | Richter |
| 6,162,243 A | 12/2000 | Gray et al. |
| 6,179,868 B1 | 1/2001 | Burpee et al. |
| 6,183,506 B1 | 2/2001 | Penn et al. |
| 6,187,034 B1 | 2/2001 | Frantzen |
| 6,190,403 B1 | 2/2001 | Fischell et al. |
| 6,200,334 B1 | 3/2001 | Jang |
| 6,206,916 B1 | 3/2001 | Furst |
| 6,217,608 B1 | 4/2001 | Penn et al. |
| 6,241,762 B1 | 6/2001 | Shanley |
| 6,258,116 B1 | 7/2001 | Hojeibane |
| 6,309,414 B1 * | 10/2001 | Rolando et al. ............. 623/1.15 |
| 6,330,884 B1 | 12/2001 | Kim |
| 6,342,067 B1 | 1/2002 | Mathis et al. |
| 6,348,065 B1 | 2/2002 | Brown et al. |
| 6,375,677 B1 | 4/2002 | Penn et al. |
| 2001/0044649 A1 | 11/2001 | Vallana et al. |
| 2001/0044652 A1 | 11/2001 | Moore |
| 2001/0044653 A1 | 11/2001 | Kveen et al. |
| 2002/0007212 A1 | 1/2002 | Brown et al. |
| 2002/0023843 A1 | 2/2002 | Cherkes |
| 2002/0032478 A1 | 3/2002 | Boekstegers et al. |
| 2002/0045933 A1 | 4/2002 | Jang |
| 2002/0045934 A1 | 4/2002 | Jang |
| 2002/0045935 A1 | 4/2002 | Jang |
| 2002/0058989 A1 | 5/2002 | Chen et al. |
| 2002/0058990 A1 | 5/2002 | Jang |
| 2002/0072792 A1 | 6/2002 | Burgermeister et al. |

FOREIGN PATENT DOCUMENTS

| | | |
|---|---|---|
| EP | 0 372 789 A3 | 6/1990 |
| EP | 0 372 7893 A3 | 6/1990 |
| EP | 0 806 190 A1 | 11/1997 |
| EP | 0 888 757 A1 | 1/1999 |
| JP | 11-104246 | 4/1999 |
| WO | WO 95/03010 | 2/1995 |
| WO | WO 97/32544 | 9/1997 |
| WO | WO 98/22159 | 5/1998 |
| WO | WO 99/17680 | 4/1999 |
| WO | WO 99/62430 | 12/1999 |
| WO | WO 00/42945 | 7/2000 |
| WO | WO 00/42946 | 7/2000 |
| WO | WO 00/62710 | 10/2000 |
| WO | WO 0062710 | 10/2000 |
| WO | WO 02/24111 A2 | 3/2002 |

OTHER PUBLICATIONS

Application for U.S. Letters U.S. Appl. No. 09/343,962, filed Jun. 20, 1999 (Pending).

* cited by examiner

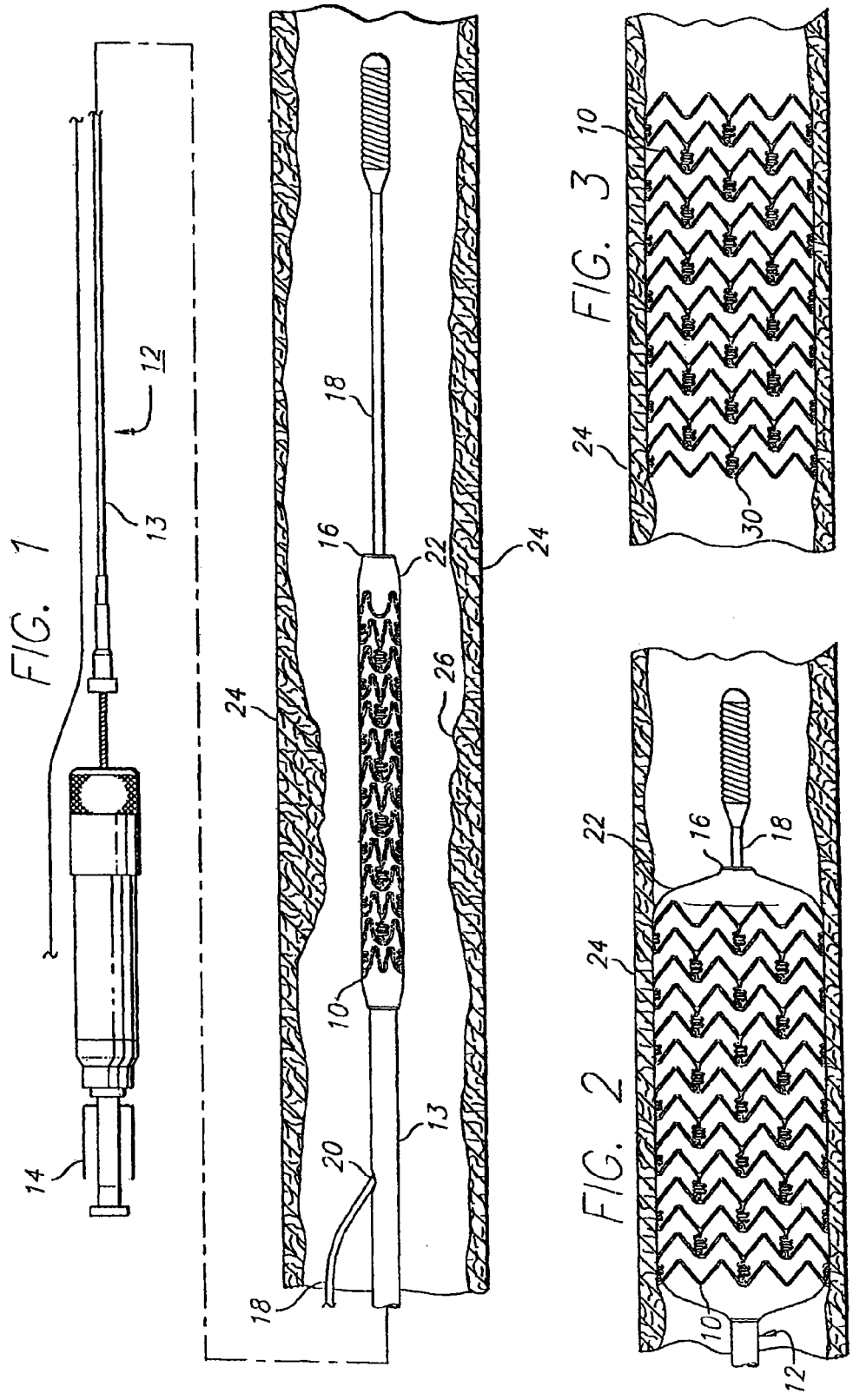

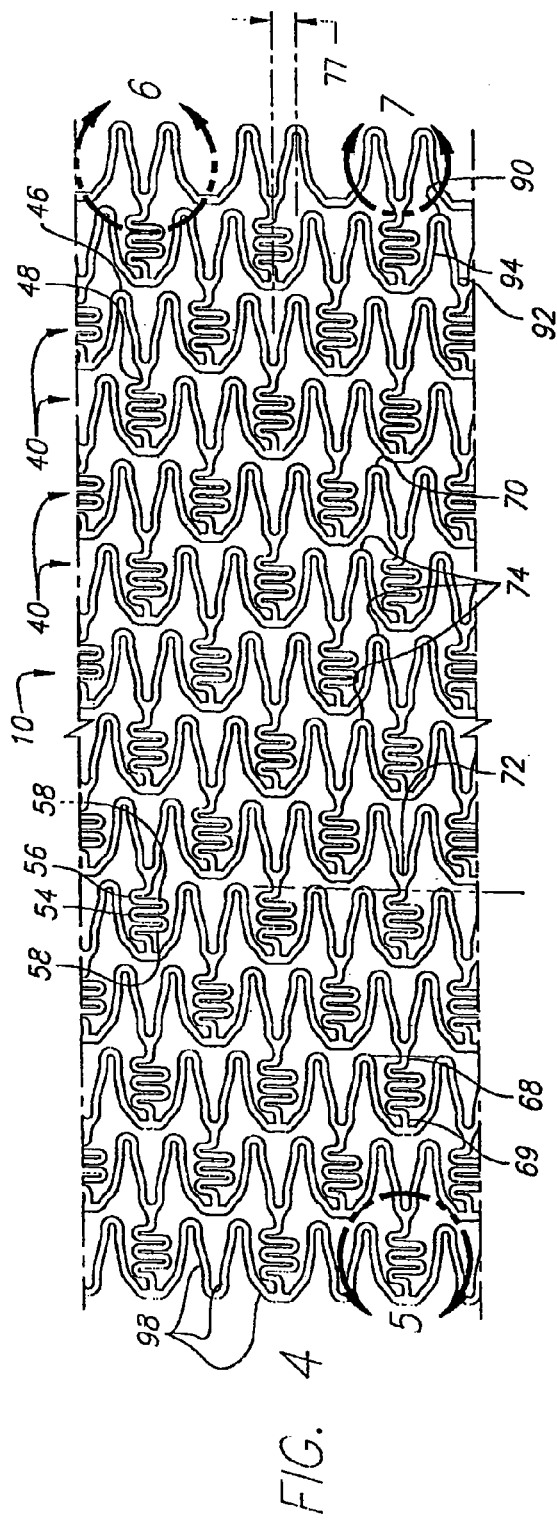
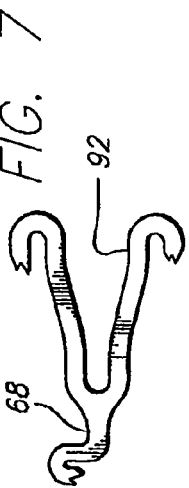
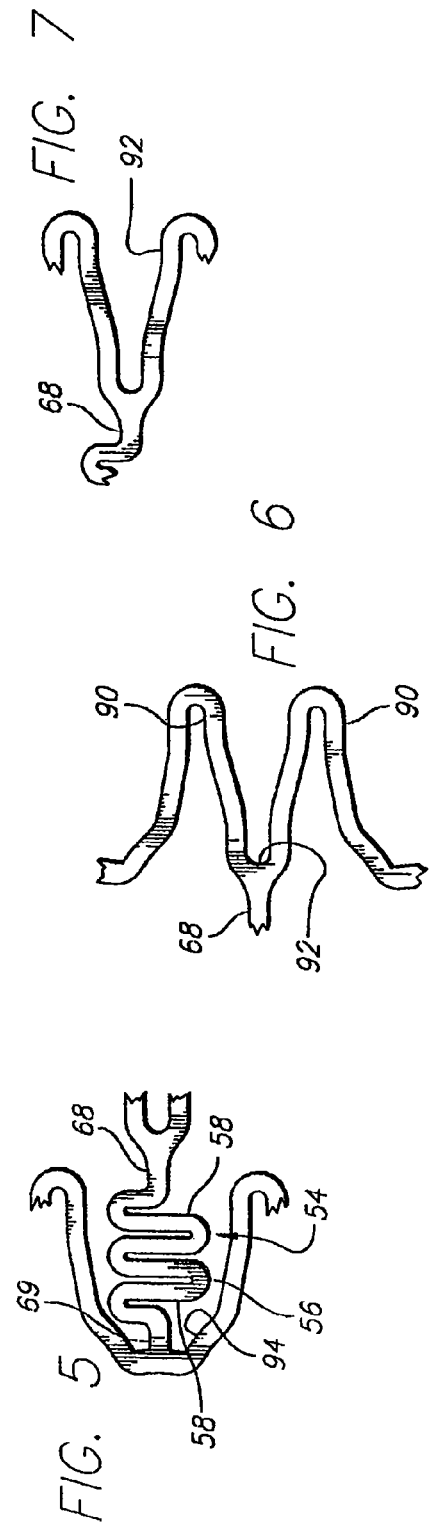

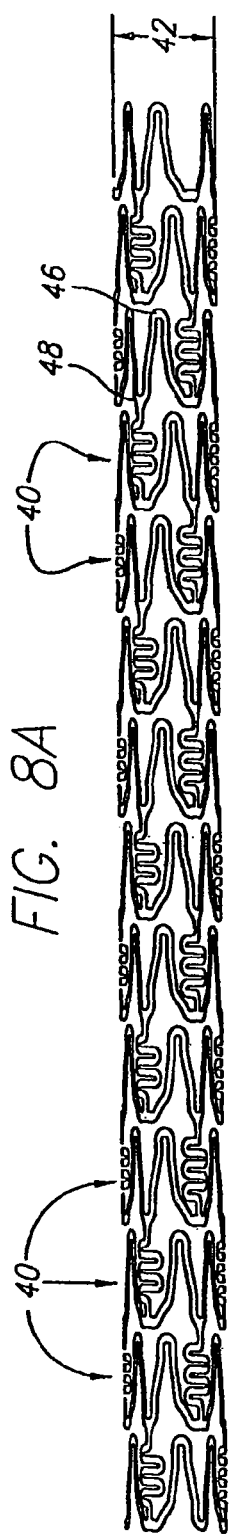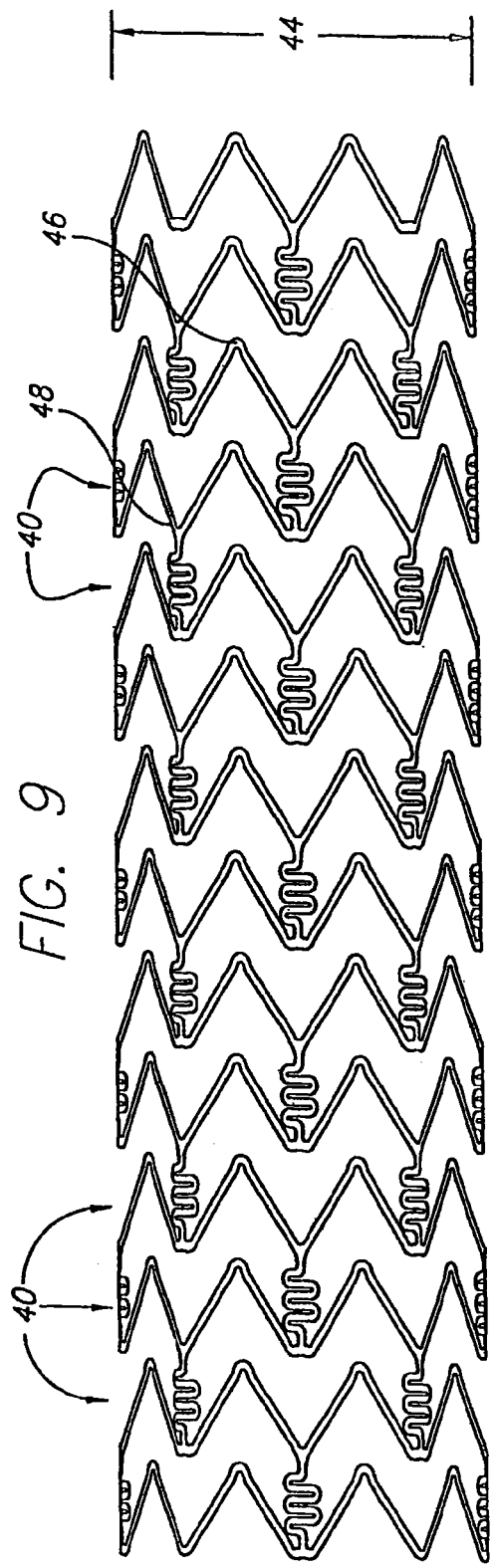

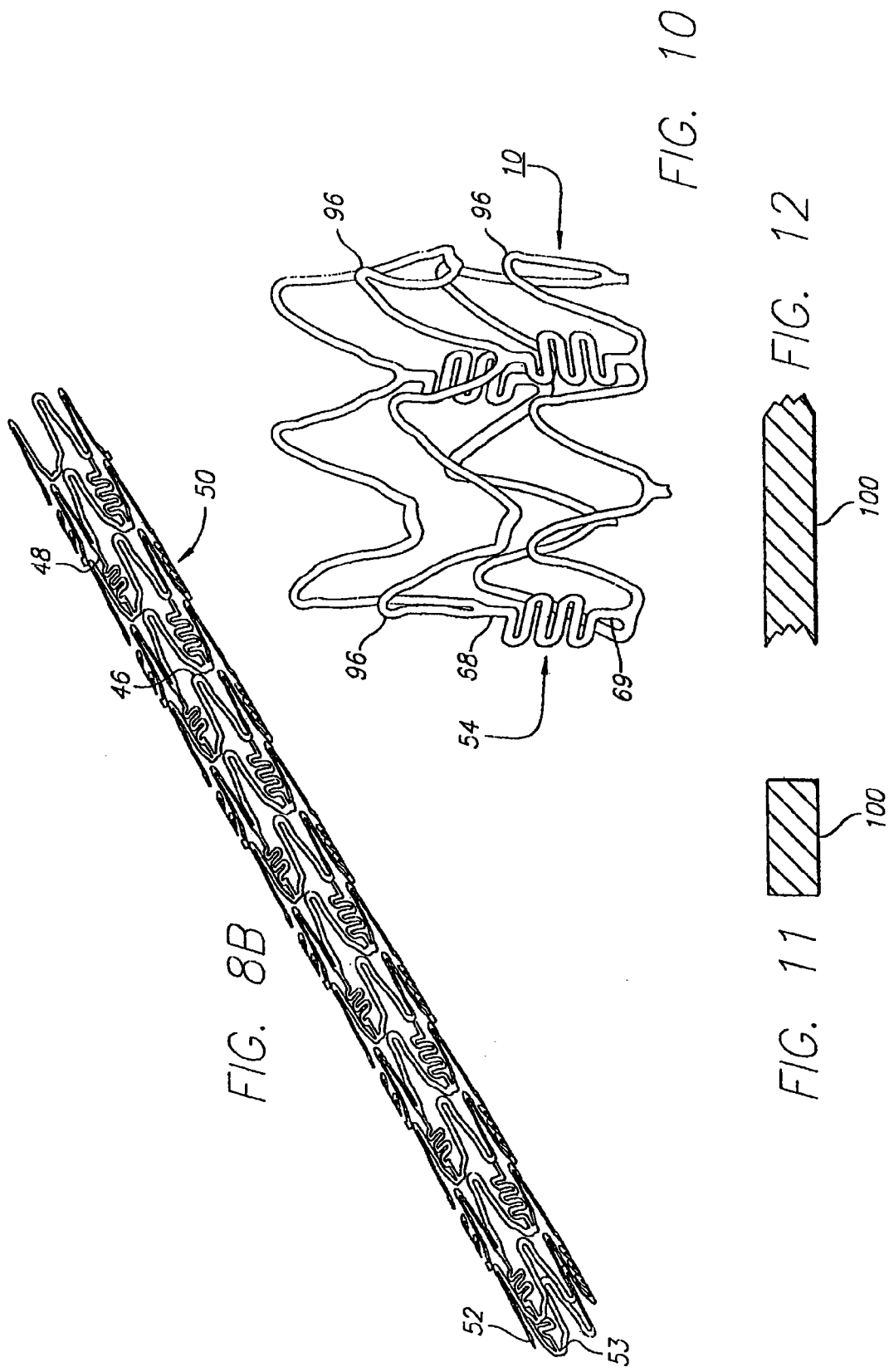

INTRAVASCULAR STENT

This Preliminary Amendment is being filed concurrently with an application that is a division of U.S. Ser. No. 10/438,687 filed May 15, 2003, which is a continuation of U.S. Ser. No. 09/564,151 filed May 3, 2000, which issued as U.S. Pat. No. 6,616,689, the entirety of which are incorporated herein by reference.

BACKGROUND OF THE INVENTION

This invention relates to vascular repair devices, and in particular intravascular stents, which are adapted to be implanted into a patient's body lumen, such as a blood vessel or coronary artery, to maintain the patency thereof. Stents are particularly useful in the treatment of atherosclerotic stenosis in arteries and blood vessels.

Stents are generally tubular-shaped devices which function to hold open a segment of a blood vessel or other body lumen such as a coronary artery. They also are suitable for use to support and hold back a dissected arterial lining that can occlude the fluid passageway. At present, there are numerous commercial stents being marketed throughout the world. While some of these stents are flexible and have the appropriate radial rigidity needed to hold open a vessel or artery, there typically is a tradeoff between flexibility and radial strength. What has been needed and heretofore unavailable is a stent which has a high degree of flexibility so that it can be advanced through tortuous passageways and can be readily expanded, and yet have the mechanical strength to hold open the body lumen or artery into which it is implanted and provide adequate vessel wall coverage. The present invention satisfies this need. That is, the stent of the present invention has a high degree of flexibility making it possible to advance the stent easily through tortuous arteries, yet the stent has sufficient radial rigidity so that it can hold open an artery or other blood vessel, or tack up a dissected lining and provide adequate vessel wall coverage.

SUMMARY OF THE INVENTION

The present invention is directed to an intravascular stent which is highly flexible along its longitudinal axis to facilitate delivery through tortuous body lumens, but which is stiff and stable enough radially in its expanded condition to maintain the patency of a body lumen such as an artery when the stent is implanted therein.

The stent of the present invention generally includes a plurality of cylindrical rings that are interconnected to form the stent. The stent typically is mounted on a balloon catheter if it is balloon expandable or mounted on a catheter without a balloon if it is self expanding.

Each of the cylindrical rings making up the stent have a proximal end and a distal end and a cylindrical plane defined by a cylindrical outer wall surface that extends circumferentially between the proximal end and the distal end of the cylindrical ring. The cylindrical rings are interconnected by at least one undulating link which attaches one cylindrical ring to an adjacent cylindrical ring. The undulating links are highly flexible and allow the stent to be highly flexible along its longitudinal axis. The undulating links are positioned substantially within the cylindrical plane of the outer wall surface of the cylindrical rings. The design of the highly flexible interconnecting members and their placement nested within a W-shaped member provides for uniform scaffolding and a high degree of vessel wall coverage.

The undulating links may take various configurations but in general have a undulating or serpentine shape. The undulating links can include bends connected by substantially straight portions wherein the substantially straight portions are substantially perpendicular to the stent longitudinal axis.

Not only do the undulating links that interconnect the cylindrical rings provide flexibility to the stent, but the positioning of the links also enhances the flexibility by allowing uniform flexibility when the stent is bent in any direction along its longitudinal axis. Further, the cylindrical rings are configured to provide flexibility to the stent in that portions of the rings can flex or bend and tip outwardly as the stent is delivered through a tortuous vessel.

The cylindrical rings typically are formed of a plurality of peaks and valleys, where the valleys of one cylindrical ring are circumferentially offset from the valleys of an adjacent cylindrical ring. In this configuration, at least one undulating link attaches each cylindrical ring to an adjacent cylindrical ring so that the undulating links are positioned substantially within one of the valleys and it attaches the valley to an adjacent peak.

While the cylindrical rings and undulating links generally are not separate structures, they have been conveniently referred to as rings and links for ease of identification. Further, the cylindrical rings can be thought of as comprising a series of U's, W's and Y-shaped structures in a repeating pattern. Again, while the cylindrical rings are not divided up or segmented into U's, W's and Y's, the pattern of the cylindrical rings resemble such configuration. The U's, W's and Y's promote flexibility in the stent primarily by flexing and by tipping radially outwardly as the stent is delivered through a tortuous vessel.

The undulating links are positioned so that the undulating portion is within the curved part of the W-shaped portion which generally increases the amount of vessel wall coverage. Since the undulating portion does not substantially expand (if at all) when the stent is expanded, it will continue to provide good vessel wall coverage even as the curved part of the W-shaped portion spreads apart as the stent is expanded.

The cylindrical rings of the stent are plastically deformed when expanded when the stent is made from a metal that is balloon expandable. Typically, the balloon-expandable stent is made from a stainless steel alloy or similar material.

Similarly, the cylindrical rings of the stent expand radially outwardly when the stent is formed from a superelastic alloy, such as nickel titanium (NiTi) alloys. In the case of superelastic alloys, the stent expands upon application of a temperature change or when a stress is relieved, as in the case of a pseudoelastic phase change.

The number and location of undulating links that interconnect adjacent cylindrical rings can be varied as the application requires. Since the undulating links typically do not expand when the cylindrical rings of the stent expand radially outwardly, the links continue to provide flexibility and to also provide a scaffolding function to assist in holding open the artery. Importantly, the addition or removal of the undulating links has very little impact on the overall longitudinal flexibility of the stent. Each undulating link is configured so that it promotes flexibility whereas prior art links actually reduce flexibility of the stent.

Because of the undulating configuration of the links, the stent has a high degree of flexibility along the stent axis, which reduces the tendency of stent fishscaling. Stent fishscaling can occur when the stent is bent and portions of the stent project outward when the stent is in the unexpanded condition. The present invention undulating links reduce the likelihood of fishscaling.

Further, because of the positioning of the links, and the fact that the links do not expand or stretch when the stent is radially expanded, the overall length of the stent is substantially the same in the unexpanded and expanded configurations. In other words, the stent will not substantially shorten upon expansion.

The stent may be formed from a tube by laser cutting the pattern of cylindrical rings and undulating links in the tube. The stent also may be formed by laser cutting a flat metal sheet in the pattern of the cylindrical rings and links, and then rolling the pattern into the shape of the tubular stent and providing a longitudinal weld to form the stent.

BRIEF DESCRIPTION OF THE DRAWINGS

FIG. 1 is an elevational view, partially in section, of a stent embodying features of the invention and which is mounted on a rapid-exchange delivery catheter and positioned within an artery.

FIG. 2 is an elevational view, partially in section, similar to that shown in FIG. 1 wherein the stent is expanded within the artery, so that the stent embeds within the arterial wall.

FIG. 3 is an elevational view, partially in section, showing the expanded stent implanted within the artery after withdrawal of the rapid-exchange delivery catheter.

FIG. 4 is a plan view of a flattened stent of the invention which illustrates the pattern of the stent shown in FIGS. 1-3.

FIG. 5 is an enlarged view of a portion of the stent shown in FIG. 4 depicting an undulating link connecting portions of adjacent cylindrical rings.

FIG. 6 is an enlarged sectional view of FIG. 4 depicting several peaks of a cylindrical ring.

FIG. 7 is an enlarged sectional view of FIG. 4 depicting a Y-shaped portion of the cylindrical ring.

FIG. 8A is a side view of a stent embodying features of the invention in an unexpanded state.

FIG. 8B is a perspective view of the stent of FIG. 8A depicting the cylindrical wall defined by each cylindrical ring.

FIG. 9 is a perspective view of the stent of FIG. 8A in an expanded condition.

FIG. 10 is a perspective view of the stent of FIG. 9 depicting projecting edges that project radially outwardly from the cylindrical wall.

FIG. 11 is a cross-sectional view of any strut of the stent.

FIG. 12 is a cross-sectional view of any strut of the stent.

DETAILED DESCRIPTION OF THE PREFERRED EMBODIMENTS

Figure 13:
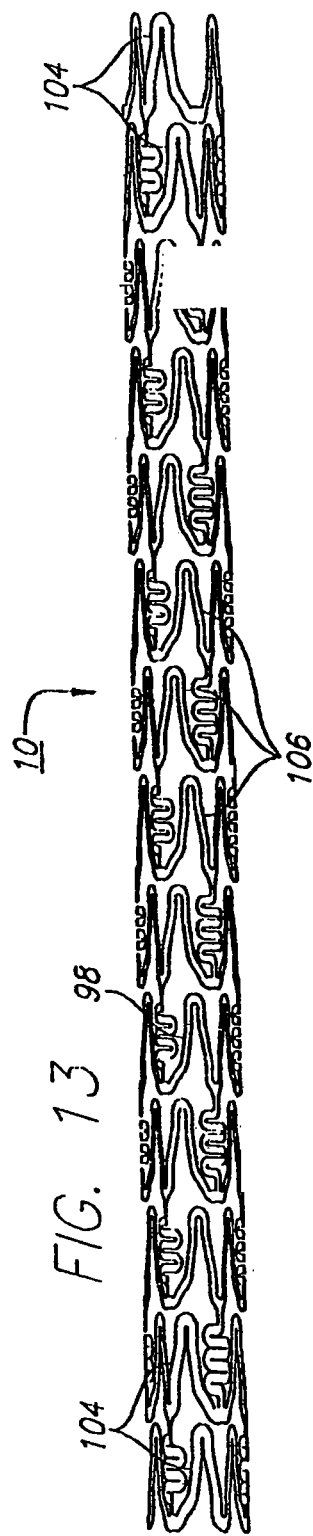
FIG. 13 is a side view of the stent depicting cylindrical rings at the end of the stent having a thicker cross-section than the rings at the center of the stent.

The present invention stent improves on existing stents by providing a longitudinally flexible stent having a uniquely designed pattern and novel interconnecting members. In addition to providing longitudinal flexibility, the stent of the present invention also provides radial rigidity and a high degree of scaffolding of a vessel wall, such as a coronary artery. The design of the highly flexible interconnecting members and their placement nested within a W-shaped member provides for uniform scaffolding and a high degree of vessel wall coverage.

Turning to the drawings, FIG. 1 depicts the present invention stent 10 mounted on a catheter assembly 12 which is used to deliver the stent and implant it in a body lumen, such as a coronary artery, peripheral artery, or other vessel or lumen within the body. The catheter assembly includes a catheter shaft 13 which has a proximal end 14 and a distal end 16. The catheter assembly is configured to advance through the patient's vascular system by advancing over a guide wire by any of the well known methods of an over the wire system (not shown) or a well known rapid exchange catheter system, such as the one shown in FIG. 1.

Catheter assembly 12 as depicted in FIG. 1 is of the well known rapid exchange type which includes an RX port 20 where the guide wire 18 will exit the catheter. The distal end of the guide wire 18 exits the catheter distal end 16 so that the catheter advances along the guide wire on a section of the catheter between the RX port 20 and the catheter distal end 16. As is known in the art, the guide wire lumen which receives the guide wire is sized for receiving various diameter guide wires to suit a particular application. The stent is mounted on the expandable member 22 (balloon) and is crimped tightly thereon so that the stent and expandable member present a low profile diameter for delivery through the arteries.

As shown in FIG. 1, a partial cross-section of an artery 24 is shown with a small amount of plaque that has been previously treated by an angioplasty or other repair procedure. Stent 10 of the present invention is used to repair a diseased or damaged arterial wall which may include the plaque 26 as shown in FIG. 1, or a dissection, or a flap which are commonly found in the coronary arteries, peripheral arteries and other vessels.

In a typical procedure to implant stent 10, the guide wire 18 is advanced through the patient's vascular system by well known methods so that the distal end of the guide wire is advanced past the plaque or diseased area 26. Prior to implanting the stent, the cardiologist may wish to perform an angioplasty procedure or other procedure (i.e., atherectomy) in order to open the vessel and remodel the diseased area. Thereafter, the stent delivery catheter assembly 12 is advanced over the guide wire so that the stent is positioned in the target area. The expandable member or balloon 22 is inflated by well known means so that it expands radially outwardly and in turn expands the stent radially outwardly until the stent is apposed to the vessel wall. The expandable member is then deflated and the catheter withdrawn from the patient's vascular system. The guide wire typically is left in the lumen for post-dilatation procedures, if any, and subsequently is withdrawn from the patient's vascular system. As depicted in FIGS. 2 and 3, the balloon is fully inflated with the stent expanded and pressed against the vessel wall, and in FIG. 3, the implanted stent remains in the vessel after the balloon has been deflated and the catheter assembly and guide wire have been withdrawn from the patient.

The stent 10 serves to hold open the artery after the catheter is withdrawn, as illustrated by FIG. 3. Due to the formation of the stent from an elongated tubular member, the undulating components of the stent are relatively flat in transverse cross-section, so that when the stent is expanded, it is pressed into the wall of the artery and as a result does not interfere with the blood flow through the artery. The stent is pressed into the wall of the artery and will eventually be covered with endothelial cell growth which further minimizes blood flow interference. The undulating portion of the stent provides good tacking characteristics to prevent stent movement within the artery. Furthermore, the closely spaced cylindrical elements at regular intervals provide uniform support for the wall of the artery, and consequently are well adapted to tack up and hold in place small flaps or dissections in the wall of the artery, as illustrated in FIGS. 2 and 3.

In keeping with the present invention, FIGS. 4-10 depict stent 10 in various configurations. Turning to FIG. 4, stent 10 is shown in a flattened condition so that the pattern can be clearly viewed, even though the stent is never in this form. The stent is typically formed from a tubular member, however, it can be formed from a flat sheet such as shown in FIG. 4 and rolled into a cylindrical configuration.

As shown in FIGS. 4-7, stent 10 is made up of a plurality of cylindrical rings 40 which extend circumferentially around the stent when it is in a tubular form (see FIG. 8). The stent has a delivery diameter 42 as shown in FIG. 8, and an implanted diameter 44 as shown in FIG. 9. Each cylindrical ring 40 has a cylindrical ring proximal end 46 and a cylindrical ring distal end 48. Typically, since the stent is laser cut from a solid tube there are no discreet parts such as the described cylindrical rings. However, it is beneficial for identification and reference to various parts to refer to the cylindrical rings and the following parts of the stent.

Each cylindrical ring 40 defines a cylindrical plane 50 which is a plane defined by the proximal and distal ends 46, 48 and the circumferential extent as the cylindrical ring travels around the cylinder. Each cylindrical ring includes cylindrical outer wall surface 52 which defines the outermost surface of the stent, and cylindrical inner wall surface 53 which defines the innermost surface of the stent. Cylindrical plane 50 follows the cylindrical outer wall surface.

In keeping with the invention, undulating link 54 is positioned within cylindrical plane 50. The undulating links connect one cylindrical ring to an adjacent cylindrical ring and provide overall longitudinal flexibility to the stent due to their unique construction. The flexibility of undulating links derives in part from bends 56 connected to straight portions 58 wherein the straight portions are substantially perpendicular to the longitudinal axis of the stent. Thus, as the stent is being delivered through a tortuous vessel, such as a coronary artery, the bends 56 and straight portions 58 of the undulating links will permit the stent to flex in the longitudinal direction which substantially enhances delivery of the stent to the target site. The number of bends and straight portions can be increased or decreased from that shown, to achieve differing flexibility constructions. With the straight portions being substantially perpendicular to the stent longitudinal axis, the undulating link acts like a hinge to provide flexibility. A straight link that is parallel to the stent axis typically is not flexible and does not add to the flexibility of the stent.

Cylindrical rings 40 can be nested such that adjacent rings slightly overlap in the longitudinal direction so that one ring is slightly nested within the next ring and so on. The degree of nesting is dictated primarily by the length of each cylindrical ring, the number of undulations in the rings, the thickness of the struts that make up the rings, and the radius of curvature, all in conjunction with the crimped or delivery diameter of the stent. If the rings are substantially nested one within the other, it may be difficult to crimp the stent to an appropriate delivery diameter without the various struts overlapping. It is also contemplated that the rings are slightly nested even after the stent is expanded, which enhances vessel wall coverage. In some circumstances, it may not be desirable to nest one ring within the other, which is also contemplated by the invention.

Referring to FIGS. 4-9, the stent 10 can be described more particularly as having a plurality of peaks 70 and valleys 72. Although the stent is not divided into separate elements, for ease of discussion references to peaks and valleys is appropriate. The number of peaks and valleys, sometimes referred to as crowns, can vary in number for each ring depending upon the application. Thus, for example, if the stent is to be implanted in a coronary artery, a lesser number of peaks and valleys (or crowns) are required than if the stent is implanted in a peripheral artery, which has a larger diameter than a coronary artery. As can be seen in FIG. 4, peaks 70 are in phase 74, meaning that the peaks 70 are substantially aligned along the longitudinal axis of the stent. It may be desirable under certain circumstances to position peaks 70 so that they are out of phase (not shown), that is, the peaks of one ring would be circumferentially offset from the peaks of an adjacent ring. As shown in FIG. 4, the peaks are circumferentially offset 77 from the valleys and from the undulating link 54. Positioning the peaks, valleys, and undulating links in this manner, provides a stent having uniform expansion capabilities, high radial strength, a high degree of flexibility, and sufficient wall coverage to support the vessel.

Referring to FIGS. 5-7, the stent of the invention can be described as having cylindrical rings formed of U-shaped portions 90, Y-shaped portions 92, and W-shaped portions 94. Again, while the stent is generally laser cut from a solid tube and it typically has no discreet parts, for ease of identification the stent of the invention also can be referred to as having U-, Y-, and W-shaped portions. The U-shaped portions have not supporting structure attached thereto. The Y-shaped portions, at their base, or apex, have arm 68 extending therefrom and attached to undulating link 54. The W portion has at its base or curve portion arm 69 which attaches at the other end of the undulating link. The length of the arms attaching the links to the rings can vary. Importantly, the arms should be sized in conjunction with the undulating link so that the link is properly positioned in the W-shaped portion. Preferably, undulating link 54 is contained within W-shaped portion 94, which should be wide enough to accommodate the undulating link when the stent is crimped so that no portion of the undulating link and the W-portion overlap. Preferably, the undulating link and the W-shaped portion are in the same cylindrical plane 50 as defined by the cylindrical outer wall surface 52 and the cylindrical inner wall surface 53.

As shown in FIG. 10, under certain stent configurations portions of the stent may project radially outwardly when the stent is expanded from its delivery diameter where it is crimped on the balloon to its expanded diameter when it is implanted in the vessel or artery. For example, as shown in FIGS. 4, 11 and 12, when a strut 98 (any section of the stent) has an equal width and thickness, projecting edges 96 likely will form when the stent is expanded from its delivery diameter to its implanted diameter. Typically, however, no projecting edges will form when a variable thickness strut is used, that is when the strut is thinner than it is wide. Thus, when a rectangular strut 100 forms the stent, as shown in FIGS. 11 and 12, it is expected that no projecting edges will form upon expansion for this particular stent pattern.

In one aspect of the invention, the stent is formed so that the struts 98 (FIG. 13) have variable thickness along the stent length. As one example, it is contemplated that struts 104 at the ends of the stent may be thicker than the struts 106 in the center of the stent for purposes for radiopacity and to counter balloon expansion. When the balloon first inflates, the balloon ends have a tendency to inflate at a faster rate than the balloon center, however, with thicker struts at the stent ends the balloon, and hence the stent, will expand more uniformly.

Figure 14:
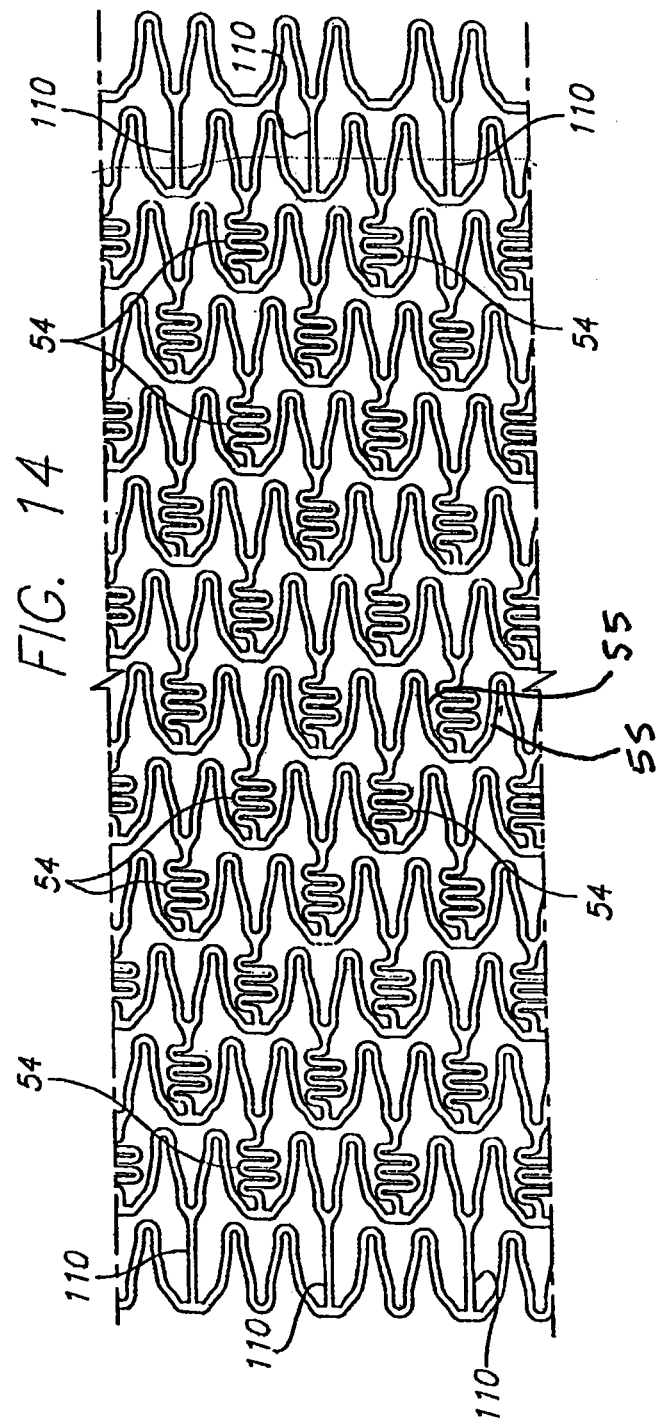
FIG. 14 is a plan view of a flattened stent of the invention illustrating a combination of undulating links and straight links.

As described above, it is also contemplated that more or fewer undulating links 54 will be positioned between adjacent cylindrical rings 40. It is also contemplated, in order to increase stent stability, that straight links 110, as shown in FIG. 14, in addition to undulating links 54, connect adjacent cylindrical rings. The straight links will provide stability and assist in preventing stent foreshortening, as do the undulating links. Further, the straight links may provide more rigidity in a localized area, such as at the stent ends, such that it may be desirable to incorporate more straight links between the cylindrical rings at the stent ends, than in the center of the stent.

In one important aspect of the invention, after stent 10 is implanted in a coronary artery, or other vessel, because of its novel design, the cylindrical rings 40 have the ability to flex radially as the vessel pulsates when blood pumps through it. Likewise, because of the novel and unique design of undulating links 54, as the vessel moves and pulsates from the pumping blood, the stent can flex longitudinally. The radial and longitudinal flexing of the stent reduces the likelihood that the stent will cause injury to the intima of a coronary artery, which also may have a tendency to reduce the likelihood of restenosis.

The stent 10 of the present invention can be made in many ways. One method of making the stent is to cut a thin-walled tubular member, such as stainless steel tubing to remove portions of the tubing in the desired pattern for the stent, leaving relatively untouched the portions of the metallic tubing which are to form the stent. In accordance with the invention, it is preferred to cut the tubing in the desired pattern by means of a machine-controlled laser as is well known in the art.

The tubing may be made of suitable biocompatible material such as stainless steel. The stainless steel tube may be Alloy type: 316L SS, Special Chemistry per ASTM F138-92 or ASTM F139-92 grade 2. Special Chemistry of type 316L per ASTM F138-92 or ASTM F139-92 Stainless Steel for Surgical Implants in weight percent.

| | |
|---|---|
| Carbon (C) | 0.03% max. |
| Manganese (Mn) | 2.00% max. |
| Phosphorous (P) | 0.025% max. |
| Sulphur (S) | 0.010% max. |
| Silicon (Si) | 0.75% max. |
| Chromium (Cr) | 17.00-19.00% |
| Nickel (Ni) | 13.00-15.50% |
| Molybdenum (Mo) | 2.00-3.00% |
| Nitrogen (N) | 0.10% max. |
| Copper (Cu) | 0.50% max. |
| Iron (Fe) | Balance |

The stent diameter is very small, so the tubing from which it is made must necessarily also have a small diameter. Typically the stent has an outer diameter on the order of about 0.06 inch in the unexpanded condition, the same outer diameter of the tubing from which it is made, and can be expanded to an outer diameter of 0.1 inch or more. The wall thickness of the tubing is about 0.003 inch.

The tubing is mounted in a rotatable collet fixture of a machine-controlled apparatus for positioning the tubing relative to a laser. According to machine-encoded instructions, the tubing is rotated and moved longitudinally relative to the laser which is also machine controlled. The laser selectively removes the material from the tubing by ablation and a pattern is cut into the tube. The tube is therefore cut into the discrete pattern of the finished stent.

The process of cutting a pattern for the stent into the tubing is automated except for loading and unloading the length of tubing. In one example, a CNC-opposing collet fixture 22 for axial rotation of the length of tubing is used in conjunction with a CNC X/Y table 25 to move the length of tubing axially relatively to a machine-controlled laser. The entire space between collets can be patterned using the $CO_2$ laser set-up of the foregoing example. The program for control of the apparatus is dependent on the particular configuration used and the pattern to be ablated in the coating.

Cutting a fine structure (0.0035" web width) requires minimal heat input and the ability to manipulate the tube with precision. It is also necessary to support the tube yet not allow the stent structure to distort during the cutting operation. In order to successfully achieve the desired end results, the entire system must be configured very carefully. The tubes are made typically of stainless steel with an outside diameter of 0.060" to 0.066" and a wall thickness of 0.002" to 0.004". These tubes are fixtured under a laser and positioned utilizing a CNC to generate a very intricate and precise pattern. Due to the thin wall and the small geometry of the stent pattern (0.0035" typical web width), it is necessary to have very precise control of the laser, its power level, the focused spot size, and the precise positioning of the laser cutting path.

In order to minimize the heat input into the stent structure, which prevents thermal distortion, uncontrolled burn out of the metal, and metallurgical damage due to excessive heat, and thereby produce a smooth debris free cut, a Q-switched Nd-YAG, typically available from Quantronix of Hauppauge, N.Y., that is frequency doubled to produce a green beam at 532 nanometers is utilized. Q-switching produces very short pulses (<100 nS) of high peak powers (kilowatts), low energy per pulse ($\leqq 3$ mJ), at high pulse rates (up to 40 kHz). The frequency doubling of the beam from 1.06 microns to 0.532 microns allows the beam to be focused to a spot size that is 2 times smaller, therefore increasing the power density by a factor of 4 times. With all of these parameters, it is possible to make smooth, narrow cuts in the stainless tubes in very fine geometries without damaging the narrow struts that make up to stent structure. Hence, the system of the present invention makes it possible to adjust the laser parameters to cut narrow kerf width which will minimize the heat input into the material.

The positioning of the tubular structure requires the use of precision CNC equipment such as that manufactured and sold by Anorad Corporation. In addition, a unique rotary mechanism has been provided that allows the computer program to be written as if the pattern were being cut from a flat sheet. This allows both circular and linear interpolation to be utilized in programming. Since the finished structure of the stent is very small, a precision drive mechanism is required that supports and drives both ends of the tubular structure as it is cut. Since both ends are driven, they must be aligned and precisely synchronized, otherwise the stent structure would twist and distort as it is being cut.

The optical system which expands the original laser beam, delivers the beam through a viewing head and focuses the beam onto the surface of the tube, incorporates a coaxial gas jet and nozzle that helps to remove debris from the kerf and cools the region where the beam interacts with the material as the beam cuts and vaporizes the metal. It is also necessary to block the beam as it cuts through the top surface of the tube and prevent the beam, along with the molten metal and debris from the cut, from impinging on the opposite surface of the tube.

In addition to the laser and the CNC positioning equipment, the optical delivery system includes a beam expander to increase the laser beam diameter, a circular polarizer, typically in the form of a quarter wave plate, to eliminate polarization effects in metal cutting, provisions for a spatial filter, a binocular viewing head and focusing lens, and a coaxial gas jet that provides for the introduction of a gas stream that surrounds the focused beam and is directed along the beam axis. The coaxial gas jet nozzle (0.018" I.D.) is centered around the focused beam with approximately 0.010" between the tip of the nozzle and the tubing. The jet is pressurized with oxygen at 20 psi and is directed at the tube with the focused laser beam exiting the tip of the nozzle (0.018" dia.). The oxygen reacts with the metal to assist in the cutting process very similar to oxyacetylene cutting. The focused laser beam acts as an ignition source and controls the reaction of the oxygen with the metal. In this manner, it is possible to cut the material with a very fine kerf with precision. In order to prevent burning by the beam and/or molten slag on the far wall of the tube I.D., a stainless steel mandrel (approx. 0.034" dia.) is placed inside the tube and is allowed to roll on the bottom of the tube as the pattern is cut. This acts as a beam/debris block protecting the far wall I.D.

Alternatively, this may be accomplished by inserting a second tube inside the stent tube which has an opening to trap the excess energy in the beam which is transmitted through the kerf along which collecting the debris that is ejected from the laser cut kerf. A vacuum or positive pressure can be placed in this shielding tube to remove the collection of debris.

Another technique that could be utilized to remove the debris from the kerf and cool the surrounding material would be to use the inner beam blocking tube as an internal gas jet. By sealing one end of the tube and making a small hole in the side and placing it directly under the focused laser beam, gas pressure could be applied creating a small jet that would force the debris out of the laser cut kerf from the inside out. This would eliminate any debris from forming or collecting on the inside of the stent structure. It would place all the debris on the outside. With the use of special protective coatings, the resultant debris can be easily removed.

In most cases, the gas utilized in the jets may be reactive or non-reactive (inert). In the case of reactive gas, oxygen or compressed air is used. Compressed air is used in this application since it offers more control of the material removed and reduces the thermal effects of the material itself. Inert gas such as argon, helium, or nitrogen can be used to eliminate any oxidation of the cut material. The result is a cut edge with no oxidation, but there is usually a tail of molten material that collects along the exit side of the gas jet that must be mechanically or chemically removed after the cutting operation.

The cutting process utilizing oxygen with the finely focused green beam results in a very narrow kerf (approx. 0.0005") with the molten slag re-solidifying along the cut. This traps the cut out scrap of the pattern requiring further processing. In order to remove the slag debris from the cut allowing the scrap to be removed from the remaining stent pattern, it is necessary to soak the cut tube in a solution of HCL for approximately 8 minutes at a temperature of approximately 55° C. Before it is soaked, the tube is placed in a bath of alcohol/water solution and ultrasonically cleaned for approximately 1 minute to remove the loose debris left from the cutting operation. After soaking, the tube is then ultrasonically cleaned in the heated HCL for 1-4 minutes depending upon the wall thickness. To prevent cracking/breaking of the struts attached to the material left at the two ends of the stent pattern due to harmonic oscillations induced by the ultrasonic cleaner, a mandrel is placed down the center of the tube during the cleaning/scrap removal process. At completion of this process, the stent structure are rinsed in water. They are now ready for electropolishing.

The stents are preferably electrochemically polished in an acidic aqueous solution such as a solution of ELECTRO-GLO#300, sold by ELECTRO-GLO Co., Inc. in Chicago, Ill., which is a mixture of sulfuric acid, carboxylic acids, phosphates, corrosion inhibitors and a biodegradable surface active agent. The bath temperature is maintained at about 110°-1350° F. and the current density is about 0.4 to about 1.5 amps per in.$^2$. Cathode to anode area should be at least about two to one. The stents may be further treated if desired, for example by applying a biocompatible coating.

It will be apparent that both focused laser spot size and depth of focus can be controlled by selecting beam diameter and focal length for the focusing lens. It will be apparent that increasing laser beam diameter, or reducing lens focal length, reduces spot size at the cost of depth of field.

Direct laser cutting produces edges which are essentially perpendicular to the axis of the laser cutting beam, in contrast with chemical etching and the like which produce pattern edges which are angled. Hence, the laser cutting process essentially provides strut cross-sections, from cut-to-cut, which are square or rectangular, rather than trapezoidal. As depicted, cylindrical rings 40 are comprised of struts 98 which have generally rectangular cross-sections 100 when the stent is laser cut from a tubular member. The struts have generally perpendicular edges formed by the laser cut. The resulting stent structure provides superior performance.

Other methods of forming the stent of the present invention can be used, such as chemical etching; electric discharge machining; laser cutting a flat sheet and rolling it into a cylinder; and the like, all of which are well known in the art at this time.

The stent of the present invention also can be made from metal alloys other than stainless steel, such as shape memory alloys. Shape memory alloys are well known and include, but are not limited to, nickel titanium and nickel/titanium/vanadium. Any of the shape memory alloys can be formed into a tube and laser cut in order to form the pattern of the stent of the present invention. As is well known, the shape memory alloys of the stent of the present invention can include the type known as thermoelastic martensitic transformation, or display stress-induced martensite. These types of alloys are well known in the art and need not be further described here.

Importantly, a stent formed of shape memory alloys, whether the thermoelastic or the stress-induced martensite-type, can be delivered using a balloon catheter of the type described herein, or in the case of stress induced martensite, be delivered via a catheter without a balloon or a sheath catheter.

While the invention has been illustrated and described herein, in terms of its use as an intravascular stent, it will be apparent to those skilled in the art that the stent can be used in other body lumens. Further, particular sizes and dimensions, number of crowns per ring, materials used, and the like have been described herein and are provided as examples only. Other modifications and improvements may be made without departing from the scope of the invention.

What is claimed is:
1. A flexible intravascular stent for use in a body lumen, comprising:
   a plurality of cylindrical rings interconnected to form the stent, each cylindrical ring having a first delivery diameter and a second expanded diameter;
   each cylindrical ring having a proximal end and a distal end and a cylindrical wall extending circumferentially between the proximal end and the distal end of the cylindrical ring;

at least one undulating link attaching each cylindrical ring to an adjacent cylindrical ring, the undulating links being positioned substantially within the cylindrical wall of the cylindrical ring;

a W-shaped portion having curved struts positioned circumferentially adjacent to the undulating links;

each cylindrical ring being nested within an adjacent cylindrical ring; and each cylindrical ring having alternating peaks and valleys, the peaks of any one cylindrical ring being circumferentially offset from a valley and the at least one undulating link of an adjacent cylindrical ring.

2. The stent of claim 1, wherein each cylindrical ring is slightly nested within an adjacent cylindrical ring.

3. The stent of claim 1, wherein each cylindrical ring is nested within an adjacent cylindrical ring when the stent is in the first delivery diameter configuration.

4. The stent of claim 1, wherein each cylindrical ring is nested within an adjacent cylindrical ring when the stent is in the second expanded diameter configuration.

5. The stent of claim 1, wherein at least one undulating link comprises at least one bend connected to a substantially straight portion, the substantially straight portion being substantially perpendicular to the stent longitudinal axis.

6. The stent of claim 5, wherein the substantially straight portion of the at least one undulating link is perpendicular to the stent longitudinal axis when the stent is in the first delivery diameter configuration.

7. The stent of claim 5, wherein the substantially straight portion of the at least one undulating link is perpendicular to the stent longitudinal axis when the stent is in the second expanded diameter configuration.

8. The stent of claim 1, wherein at least one of the undulating links comprise a plurality of bends.

9. The stent of claim 1, wherein the undulating links are configured to provide flexibility to the stent.

10. The stent of claim 1, wherein the cylindrical rings are configured to provide flexibility to the stent.

11. The stent of claim 1, wherein the stent is formed from a tube.

12. The stent of claim 1, wherein the cylindrical rings and the undulating links are defined by a plurality of struts.

13. The stent of claim 12, wherein at least one of the struts has a varying cross-section.

14. The stent of claim 12, wherein at least one of the struts has a cross-section that is different than other struts.

15. The stent of claim 12, wherein at least some of the struts have a variable radial thickness.

16. A flexible intravascular stent for use in a body lumen, comprising:

a plurality of cylindrical rings interconnected to form the stent, each cylindrical ring having a first delivery diameter and a second expanded diameter;

each cylindrical ring having a plurality of peaks and valleys, the peaks of one cylindrical ring being circumferentially offset from the peaks of an adjacent cylindrical ring and the peaks of one cylindrical ring being circumferentially offset from the valleys of an adjacent cylindrical ring;

at least one undulating link attaching each cylindrical ring to an adjacent cylindrical ring, the at least one undulating link being positioned substantially within one of the valleys and attaching the valley to an adjacent peak; and a W-shaped portion having curved struts positioned circumferentially adjacent to the undulating links; and each cylindrical ring is nested within an adjacent cylindrical ring.

17. A flexible intravascular stent for use in a body lumen, comprising:

a plurality of cylindrical rings interconnected to form the stent, each cylindrical ring having a first delivery diameter and a second expanded diameter;

the cylindrical rings having a plurality of U-shaped portions, Y-shaped portions, and W-shaped portions that are expandable;

each cylindrical ring having a proximal end and a distal end and a cylindrical wall extending circumferentially between the proximal end and the distal end of the cylindrical ring;

at least one undulating link attaching each cylindrical ring to an adjacent cylindrical ring, the undulating links being positioned substantially within the cylindrical wall of the cylindrical ring;

each cylindrical ring having alternating peaks and valleys, the peaks of any one cylindrical ring being circumferentially offset from a valley and the at least one undulating link of an adjacent cylindrical ring;

the W-shaped portion having curved struts positioned circumferentially adjacent to the undulating links; and wherein each cylindrical ring is nested within an adjacent cylindrical ring.

* * * * *